United States Patent
Horn

(10) Patent No.: US 7,336,833 B2
(45) Date of Patent: Feb. 26, 2008

(54) DEVICE, SYSTEM, AND METHOD FOR REDUCING IMAGE DATA CAPTURED IN-VIVO

(75) Inventor: Eli Horn, Kiryat Motzkin (IL)

(73) Assignee: Given Imaging, Ltd., Yoqneam (IL)

( * ) Notice: Subject to any disclaimer, the term of this patent is extended or adjusted under 35 U.S.C. 154(b) by 493 days.

(21) Appl. No.: 10/879,284

(22) Filed: Jun. 30, 2004

(65) Prior Publication Data
US 2006/0034514 A1 Feb. 16, 2006

(51) Int. Cl.
G06K 9/36 (2006.01)
G06K 9/46 (2006.01)

(52) U.S. Cl. ...................................... 382/232
(58) Field of Classification Search ........... 382/128, 382/173, 232, 233, 299; 348/65, 76, 92; 600/109
See application file for complete search history.

(56) References Cited

U.S. PATENT DOCUMENTS

| | | | |
|---|---|---|---|
| 3,683,389 A | 8/1972 | Hollis | |
| 3,705,579 A | 12/1972 | Morini et al. | |
| 3,971,362 A | 7/1976 | Pope et al. | |
| 4,027,510 A | 6/1977 | Hiltebrandt | |
| 4,198,960 A | 4/1980 | Utsugi | |
| 4,217,045 A | 8/1980 | Ziskind | |
| 4,278,077 A * | 7/1981 | Mizumoto | 600/109 |
| 4,481,952 A | 11/1984 | Pawelec | |
| 4,588,294 A | 5/1986 | Siegmund | |
| 4,642,678 A | 2/1987 | Cok | |
| 4,689,621 A | 8/1987 | Kleinberg | |
| 4,741,327 A | 5/1988 | Yabe | |
| 4,782,819 A | 11/1988 | Adair | |
| 4,819,620 A | 4/1989 | Okutsu | |
| 4,844,076 A | 7/1989 | Lesho et al. | |
| 4,901,708 A | 2/1990 | Lee | |
| 4,905,670 A | 3/1990 | Adair | |
| 4,936,823 A | 6/1990 | Colvin et al. | |
| 4,951,135 A | 8/1990 | Sasagawa et al. | |
| 5,026,368 A | 6/1991 | Adair | |
| 5,143,054 A | 9/1992 | Adair | |
| 5,209,220 A | 5/1993 | Hiyama et al. | |
| 5,267,033 A * | 11/1993 | Hoshino | 348/92 |

(Continued)

FOREIGN PATENT DOCUMENTS

AU 2004201212 10/1999

(Continued)

OTHER PUBLICATIONS

U.S. Appl. No. 09/807,892, filed Jun. 6, 2001, Meron et al.

(Continued)

Primary Examiner—Amir Alavi
(74) Attorney, Agent, or Firm—Pearl Cohen Zedek Latzer LLP

(57) ABSTRACT

A device, system, and method for reducing image data using spatially varying reduction are described. Images may be captured from an in-vivo device, while the reduced images may be transmitted via wireless communications. Reduction may be achieved by selecting a spatial area of interest on an image frame, dividing the spatial area of interest into one or more sub-regions, reducing each sub-region by a defined reduction ratio according to the spatial properties of said sub-region, and transmitting image data from spatial area of interest.

25 Claims, 4 Drawing Sheets

U.S. PATENT DOCUMENTS

| | | |
|---|---|---|
| 5,279,607 A | 1/1994 | Schentag et al. |
| 5,331,551 A | 7/1994 | Tsuruoka et al. |
| 5,368,015 A | 11/1994 | Wilk |
| 5,373,322 A | 12/1994 | Laroche et al. |
| 5,379,757 A | 1/1995 | Hiyama et al. |
| 5,381,784 A | 1/1995 | Adair |
| 5,382,976 A | 1/1995 | Hibbard |
| 5,398,670 A | 3/1995 | Ortiz et al. |
| 5,459,605 A | 10/1995 | Kempf |
| 5,506,619 A | 4/1996 | Adams, Jr. et al. |
| 5,603,687 A | 2/1997 | Hori et al. |
| 5,604,531 A * | 2/1997 | Iddan et al. ............ 348/76 |
| 5,607,435 A | 3/1997 | Sachdeva et al. |
| 5,652,621 A | 7/1997 | Adams, Jr. et al. |
| 5,653,677 A | 8/1997 | Okada et al. |
| 5,662,587 A | 9/1997 | Grundfest et al. |
| 5,697,384 A | 12/1997 | Miyawaki et al. |
| 5,819,736 A | 10/1998 | Avny et al. |
| 5,940,126 A | 8/1999 | Kimura |
| 5,993,378 A | 11/1999 | Lemelson |
| 6,123,666 A | 9/2000 | Wrenn et al. |
| 6,184,922 B1 | 2/2001 | Saito et al. |
| 6,184,923 B1 | 2/2001 | Miyazaki |
| 6,240,312 B1 | 5/2001 | Alfano et al. |
| D457,236 S | 5/2002 | Meron et al. |
| 6,428,469 B1 | 8/2002 | Iddan et al. |
| 6,453,199 B1 | 9/2002 | Kobozev |
| 6,632,175 B1 | 10/2003 | Marshall |
| 6,709,387 B1 | 3/2004 | Glukhovsky et al. |
| D492,791 S | 7/2004 | Alexander |
| 6,918,872 B2 | 7/2005 | Yokoi et al. |
| 2001/0017649 A1 | 8/2001 | Yaron |
| 2001/0051766 A1 | 12/2001 | Gazdzinski |
| 2002/0032366 A1 | 3/2002 | Iddan et al. |
| 2002/0042562 A1 | 4/2002 | Meron et al. |
| 2002/0103417 A1 | 8/2002 | Gazdzinski |
| 2002/0107444 A1 | 8/2002 | Adler |
| 2002/0109774 A1 | 8/2002 | Meron et al. |
| 2002/0118400 A1 | 8/2002 | Kishimizu et al. |
| 2002/0177779 A1 | 11/2002 | Adler et al. |
| 2002/0198439 A1 | 12/2002 | Mizuno |
| 2003/0018280 A1 | 1/2003 | Lewkowicz et al. |
| 2003/0028078 A1 | 2/2003 | Glukhovsky |
| 2003/0043263 A1 | 3/2003 | Glukhovsky et al. |
| 2003/0045790 A1 | 3/2003 | Lewkowicz et al. |
| 2003/0077223 A1 | 4/2003 | Glukhovsky et al. |
| 2003/0114742 A1 | 6/2003 | Lewkowicz et al. |
| 2003/0117491 A1 | 6/2003 | Avni et al. |
| 2003/0120130 A1 | 6/2003 | Glukhovsky et al. |
| 2003/0151661 A1 | 8/2003 | Davidson et al. |
| 2003/0167000 A1 | 9/2003 | Mullick et al. |
| 2003/0171648 A1 | 9/2003 | Yokoi et al. |
| 2003/0171649 A1 | 9/2003 | Yokoi et al. |
| 2003/0195415 A1 | 10/2003 | Iddan |
| 2003/0208107 A1 | 11/2003 | Rafael |
| 2003/0211405 A1 | 11/2003 | Venkataraman |
| 2003/0214579 A1 | 11/2003 | Iddan |
| 2003/0214580 A1 | 11/2003 | Iddan |
| 2003/0216622 A1 | 11/2003 | Meron et al. |
| 2004/0027459 A1 | 2/2004 | Segawa et al. |
| 2004/0027500 A1 | 2/2004 | Davidson et al. |
| 2004/0073087 A1 | 4/2004 | Glukhovsky et al. |
| 2004/0087832 A1 | 5/2004 | Glukhovsky et al. |
| 2004/0138532 A1 | 7/2004 | Glukhovsky |
| 2004/0199061 A1 | 10/2004 | Glukhovsky |
| 2004/0236182 A1 | 11/2004 | Iddan et al. |
| 2004/0254455 A1 | 12/2004 | Iddan |
| 2004/0258328 A1 | 12/2004 | Adler |
| 2005/0025368 A1 | 2/2005 | Glukhovsky |
| 2005/0049461 A1 | 3/2005 | Honda et al. |
| 2006/0108506 A1 * | 5/2006 | Yang et al. ............ 250/208.1 |
| 2006/0262186 A1 * | 11/2006 | Avni et al. ............ 348/65 |

FOREIGN PATENT DOCUMENTS

| | | |
|---|---|---|
| DE | 344 0177 | 11/1984 |
| DE | 3440177 | 5/1986 |
| EP | 0 228 493 | 7/1987 |
| IL | 143259 | 5/2001 |
| JP | 57-45833 | 3/1982 |
| JP | 58-29439 | 2/1983 |
| JP | 3-289779 | 12/1991 |
| JP | 4-109927 | 4/1992 |
| JP | 4109927 | 4/1992 |
| JP | 1992-144533 | 5/1992 |
| JP | 4-180736 | 6/1992 |
| JP | 5015515 | 1/1993 |
| JP | 6-285044 | 10/1994 |
| JP | 7-289504 | 11/1995 |
| JP | 2000-342522 | 12/2000 |
| JP | 2000-342527 | 12/2000 |
| JP | 2001-137182 | 5/2001 |
| JP | 2001-224551 | 8/2001 |
| JP | 2001-224553 | 8/2001 |
| JP | 2000-342524 | 6/2002 |
| JP | 2000-342525 | 6/2002 |
| WO | WO 92/21307 | 12/1992 |
| WO | WO 96/37796 | 11/1996 |
| WO | WO 98/11816 | 3/1998 |
| WO | WO 98/51993 | 11/1998 |
| WO | WO 01/08548 | 2/2001 |
| WO | WO 01/50180 | 7/2001 |
| WO | WO 01/50941 | 7/2001 |
| WO | WO 01/65995 | 9/2001 |
| WO | WO 02/067593 | 8/2002 |
| WO | WO 03/011103 | 2/2003 |
| WO | WO 03/053241 | 7/2003 |
| WO | WO 2004/028336 | 4/2004 |
| WO | WO 2004/082472 | 9/2004 |
| WO | WO 2004/088448 | 10/2004 |
| WO | WO 2004/096008 | 11/2004 |

OTHER PUBLICATIONS

U.S. Appl. No. 10/200,548, filed Jul. 23, 2002, Glukhovsky et al.
U.S. Appl. No. 10/493,751, filed Apr. 27, 2004, Glukhovsky et al.
U.S. Appl. No. 10/166,025, filed Jun. 11, 2002, Lewkowicz et al.
U.S. Appl. No. 10/213,345, filed Aug. 7, 2002, Glukhovsky.
U.S. Appl. No. 29/196,699, filed Jan. 5, 2004, Iddan et al.
The Radio Pill, Rowlands, et al., British Communications And Electronics, Aug. 1960, pp. 598-601.
Wellesley Company Sends Body Monitors Into Space—Crum, Apr. 1998.
Wireless Transmission Of A Color Television Moving Image From The Stomach Using A Miniature CCD Camera, Light Source And Microwave Transmitter, Swain CP, Gong F, Mills TN. Gastrointest Endosc 1997; 45:AB40.
BBC News Online—Pill Camera To "Broadcast From The Gut", Feb. 21, 2000, www.news.bbc.co.uk.
Biomedical Telemetry, R. Stewart McKay, Published By John Wiley And Sons, 1970.
R. Kimmel, "Demosaicing: Image reconstruction from color ccd samples", IEEE Transactions on Image Processing, vol. 8, pp. 1221-1228, 1999.
D. D. Muresan and T.W. Parks, "Optimal Recovery approach to image interpolation", in IEEE Proc. ICIP., vol. 3, 2001 pp. 7-10.
Shin-ishi et al., "Robots for the future", pp. 1-2, Nov. 29, 2001 jp/nipponia/nipponia13/sp05.html.
Video camera to "Take", RF System Lab, 1 page, Dec. 25, 2001.
Norkia3, RF Systems Lab, pp. 1-14, http://www.rfnorika.com/, Jan. 1, 2002.
B. Guntruck, Y. Altunbasak and R. Mersereau, "Color plane interpolation using alternating projections", IEEE Transactions on Image Processing, vol. 11, No. 9 Sep. 2002, pp. 997-1013.

Wang et al., "Intergrated Micro-Instrumentation for Dynamic Monitoring of the Gastro-Intestinal Tract", www.see.ed.ac.uk/Naa Publications.html, presented at IEEE Instrumentation and Measurement Technology Conference, May 2002, Anchorage, AK, USA, pp. 1-4.

Dan Slater, Panoramic Photography with Fisheye Lenses, © 1995, Published in the IAPP Journal 1996.

New smart plastic has good memory—Turke, 1996.

International Search Report of Application No. PCT/IL05/00691 dated Sep. 6, 2006.

* cited by examiner

DEVICE, SYSTEM, AND METHOD FOR REDUCING IMAGE DATA CAPTURED IN-VIVO

FIELD OF THE INVENTION

The present invention relates to an in-vivo device, system, and method for reducing the amount of data used, stored or transmitted, such as in-vivo image data, more specifically, for reducing data prior to transmission.

BACKGROUND OF THE INVENTION

Devices, systems, and methods for performing in-vivo imaging of passages or cavities within a body, and for gathering information other than or in addition to image information (e.g., temperature information, pressure information), are known in the art. Such devices may include, inter alia, various endoscopic imaging systems, autonomous capsule image systems and devices for performing imaging in various body cavities.

An in-vivo image capture device may transmit image data through, for example, wireless channels. Reducing the amount of data per image to be transmitted may, in some systems enable faster transmission rates, lower band transmission channels, and/or larger images (more data) to be transmitted through possibly lower band transmission channels. Reducing the amount of data may, for example, be by compression, dilution, or other known methods.

Devices and systems that may use known compression algorithms such as, JPEG, MPEG, FELIX, LOCO, etc., for reducing the amount of data per image to be, for example, transmitted or stored are known in the art. Compression methods, such as these may need significant processing power or speed. An in-vivo imaging system may benefit in size and cost if the processing power or speed may be maintained at a minimum.

When capturing images with optical systems that may in some way yield spatially varying resolution due to distortion, for example, an optical system that may include a convex or other type of mirror or reflective element, or other elements that may distort a view, one region in the captured image may have a lower resolution while another region in the same captured image may have a higher resolution. Applying, for example, a single data reduction ratio, for example a preset compression ratio, over the entire spatial area of an image may result in, for example, under sampling of one part of the reduced image and over sampling of another part of the reduced image.

SUMMARY OF THE INVENTION

According to an embodiment of the present invention, there is provided a device, system, and method for reducing image data. In some embodiments of the invention, the device may be an in-vivo wide-field-of-view imaging device including, for example, an image distorting element, for example, a curved reflective element. In one embodiment of the invention, a spatially varying dilution pattern is provided, to reduce image data. In another embodiment of the invention, reduced image data may be, for example, transmitted to an external receiving unit and, for example, reconstructed.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
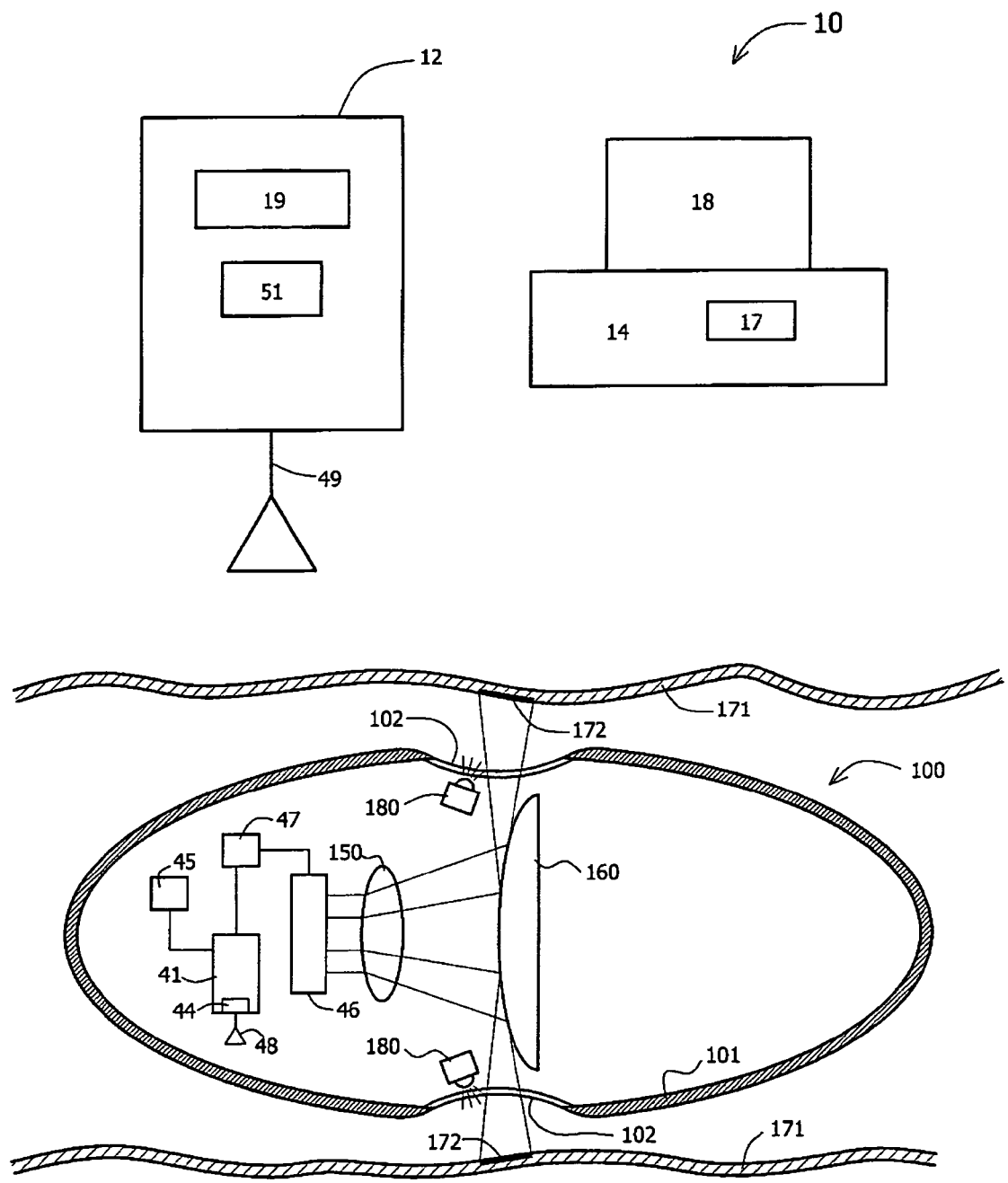
FIG. 1 is a schematic illustration of an in-vivo sensing system in accordance with some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the device, system, and method of the present invention may be typically used in conjunction with an in-vivo sensing system such as described in U.S. Pat. No. 5,604,531 to Iddan et al. and/or in International Application number WO 01/65995 entitled "A Device And System For In-Vivo Imaging", published on 13 Sep. 2001, and/or in PCT application number PCT/IL2004/000367 filed on 2 May, 2004, all of which are assigned to the common assignee of the present invention and all of which are hereby incorporated by reference. However, a device, system, and method according to various embodiments of the present invention may be used with other in-vivo systems. Alternate embodiments of the system and method of the present invention may be used with other devices, e.g. non-imaging and/or non-in-vivo devices.

Embodiments of the in-vivo device may typically be autonomous and may typically be self-contained. For example, the in-vivo device may be a capsule or another unit where all the components may be substantially contained within a container or shell, and where the in-vivo device may not require any wires or cables to, for example, receive power or transmit information. The in-vivo device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Reference is now made to FIG. 1, showing a schematic illustration of an in-vivo sensing system 10 in accordance with some embodiments of the present invention. In one embodiment, the system may include an in-vivo sensing device 100. Device 100 may typically be or may typically include an autonomous swallowable capsule, but may have other shapes, and need not be swallowable or autonomous. In some embodiment, device 100 may include, for example, an in-vivo camera that may capture and transmit, for example, images of a body lumen, for example, the GI tract while the device 100 may pass through, for example, the GI lumens. Other suitable lumens may be sensed, for example, imaged. In one embodiment of the invention, device 100 may achieve a broad field-of-view. Some embodiments may include an image distorting element, for example a curved or other suitable reflective element 160, or a combination of elements to for example capture a panoramic or near panoramic image. Other suitable distorting elements, for example a fisheye lens, or other elements may be used.

In one embodiment of the invention, device 100 may include a housing 101 with a circumferential viewing window 102, a sensor, for example, an imager 46, an optical system 150, an image distorting element, for example, a curved reflective element 160, and an illumination source 180. In one embodiment of the invention, optical system 150 may include, for example, a fisheye lens. In another embodiment, device 100 may not include a reflective element 160, and may include other suitable components. Sensors, such as spatial sensors other than image sensors may be used for sensing other types of spatial data in-vivo.

Imager 46 may include an electronic imager for capturing images. For example, imager 46 may include a Complimentary Metal Oxide Semiconductor (CMOS) electronic imager. In other embodiment of the invention, image 46 may include other suitable types of optical sensors, such as a Charged Coupled Device (CCD).

Device 100 may include a transmitter 41 and an antenna 48 for transmitting data, typically wirelessly, and a power source 45 to power device 100. In other embodiments transmission need not be wireless. Transmitter 41 may typically, in some embodiments of the invention act as a controller and may also include circuitry and functionality for controlling the device 100, although control capability or one or more aspects of control may be included in a separate component, for example, in processing unit 47. In one embodiment of the invention device 100 may include a data reduction circuit 44. Data reduction circuit 44 may include, for example, circuitry for directing the output from a preset subgroup of pixels to, for example the transmitter 41, a processing unit 47, and/or a memory unit. Data reduction circuit 44 may, in some embodiments of the invention be integral to transmitter 41. In other embodiments of the invention, data reduction circuit 44 may be integral to processing unit 47, may be a separate component or a series of components. Transmitter 41 may include processing unit 47, data reduction circuit 44, or the functionality of processing unit 47 and/or data reduction circuit 44. In one embodiment, transmitter 41, and processing unit 47 and data reduction circuit 44, if they are separate units, are application specific integrated circuits (ASIC), but in other embodiments other types of processors may be used. For example, processing units may include a processor executing instructions.

In one embodiment, all of the components may be sealed within the device body (the body or shell may include more than one piece); for example, an imager 46, illumination source 180, power source 45, and transmitting and control units, for example transmitter 41, may all be sealed within the device body 100.

In one exemplary embodiment, each frame of image data may include, for example, 256 rows of 256 pixels each, where each pixel may include data for color and brightness, according to known methods. In another exemplary embodiment of the invention, each frame of image data may include, for example, 512 rows of 512 pixels each, and each pixel may include data for color and brightness, according to known methods. Other suitable number pixels and geometries may be used. Other suitable data formats may be used. For example, in each pixel color may be represented by a mosaic of four sub-pixels, each sub-pixel corresponding to primaries such as red, green, or blue (where one primary is represented twice). In other embodiments, each pixel may capture only one color. The brightness of the overall pixel may be recorded by, for example, a one byte (e.g., 0-255) brightness value. Other suitable data, and color formats may be used. For example, a black and white imager may be used.

Outside the patient's body may be receiving unit 12, for example, an external portable receiver including an antenna or an antenna array 49, a storage unit 19, and an optional receiving unit processor 51. Data recorded by the receiving unit may, in some embodiments of the invention be processed on a data processor 14, for example, in a external stationary data processor, stored in a external stationary storage unit 17, for example, in a stationary storage unit and may be, for example, displayed on an external monitor 18. Other suitable systems and methods of storing, processing and/or displaying collected data may be used. Receiving unit 12 may in some embodiments of the invention, not be portable.

In one embodiment, as device 100 may traverse, for example, a body lumen 171, device 100 may, for example, capture an image of a portion such as a "slice" of body lumen slice 172. Illumination source 180 may, for example, illuminate slice 172 of body lumen 171. The light returned from illuminated slice 172 may be deflected using, for example, reflective element 160, focused and/or transferred using optical system 150, and received by imager 46 that may thereby capture an image of slice 172. Imager 46 may, for example, capture a panoramic image (360 degrees image) or near panoramic image of slice 172 of body lumen 171. Alternatively, such image may, for example, include a non-complete image of slice 172 (less than 360 degrees).

Figure 2A:
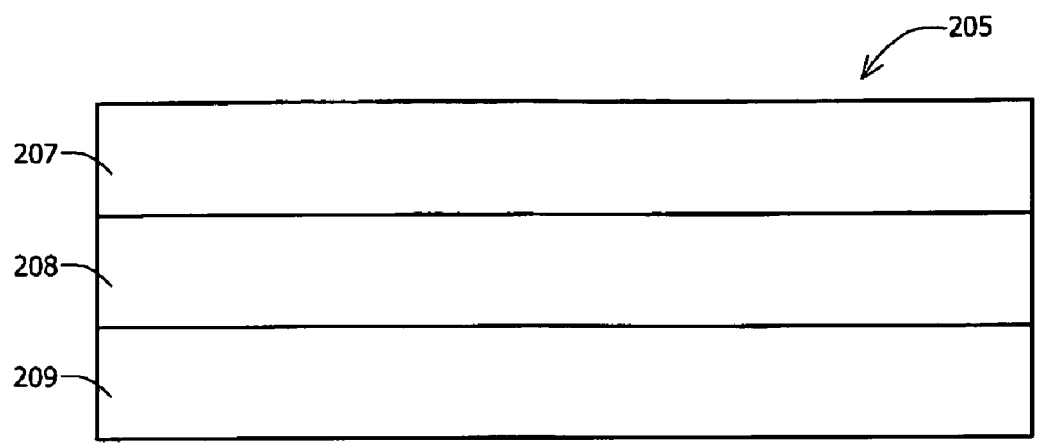
FIG. 2A is a schematic illustration of an exemplary panoramic view according to an embodiment of the present invention.

In one embodiment, slice 172 may be ring-shaped; other shapes or configurations may be used. Reference is now made to FIG. 2A showing a schematic illustration of an exemplary panoramic view, for example, a view of body lumen tissue slice 172 from a circumferential viewing window 102 (FIG. 1). Other slices and/or views, from other viewing windows may be used. In FIG. 2A, sub-regions 207, 208, and 209 are shown to have equal areas. Sub-regions 207, 208, and 209 are defined for the purpose of discussion and for easy reference to different regions in view 205. View 205 may be any view, for example, a slice of a body lumen, a panoramic view of a GI lumen, or any other suitable view. In one embodiment of the invention, circumferential slice 172 may be imaged by, for example, a single rectangular or square imager with the aid of, for example, a reflective element 160 that may direct light penetrating through, for example, a circumferential viewing window 102 toward imager 46. In some embodiments of the invention, reflective element 160 may cause distortion of the panoramic imaged view. Other views may be imaged, for example, views other than panoramic views.

Figure 2B:
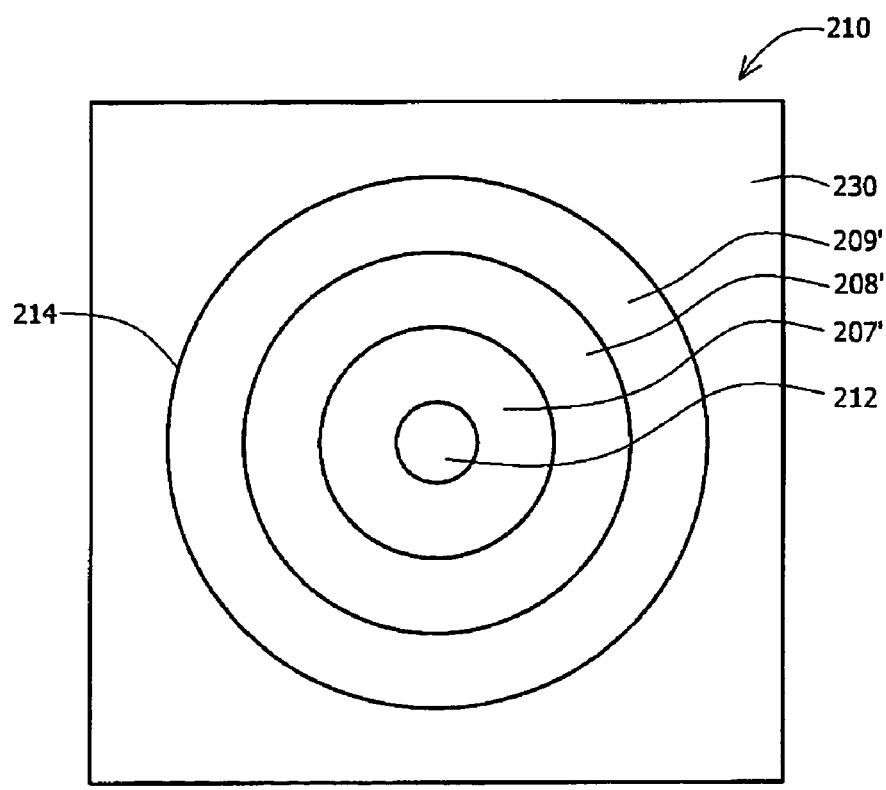
FIG. 2B is a schematic illustration of rectangular image frame with a captured panoramic view according to an embodiment of the present invention.

An image of slice 172 may be captured, for example, onto a rectangular, square, or other shaped imager. Reference is now made to FIG. 2B showing an image frame 210 of view 205 captured, for example, onto a rectangular imager, for example, imager 46. In some embodiments of the invention, frame 210 may include a distorted image of view 205. In one embodiment of the invention, frame 210 may include, for example, a panoramic disk shaped image 214 with a "hole" 212. Other suitable shapes, such as for example, a disk without a hole, a rectangle with a hole or other suitable shapes may result with alternate optical systems and imagers. Sub-regions 207', 208', and 209' in frame 210 may correspond to sub-regions 207, 208, and 209 in view 205 (FIG. 2A). Due to distortion, sub-regions 207', 208', and 209' may cover non-equal areas as opposed to sub-regions 207, 208, and 209 (FIG. 2A). For example, the area of sub-region 207' may be smaller than the area of sub-region 209'. As such, sub-region 207' may be imaged, for example, at a lower resolution, as compared to, for example, sub-region 209'. In other words, the spatial resolution in sub-region 207' may, for example, be lower than the spatial resolution in sub-region 209' as a result of the distortion.

Furthermore, in some embodiments of the invention, sub-regions 230 and 212 or other areas may, for example, not contain any image information. In some embodiments of the invention, pixels in areas 212 and 230 may, for example, not be included in a reduced image and may not, for example, be transmitted, stored, processed, etc. In addition, in one embodiment of the invention, low-resolution areas (for example sub-region 207') may, for example, be minimally reduced or not reduced at all while higher resolution areas (for example sub-region 209') may be reduced. In other embodiments, frame 210 may be of other shapes and have other spatial variations in resolution. In one embodiment of the invention, spatial variation in resolution may be due to factors, other than optical distortion. The spatial variation may be, for example, due to the nature of information imaged, or due to more than one type of information sampled by a single imager, for example, due to more than one filters placed over an imager, or due to more than one optical path with, for example, different properties directing light to different areas on a single imager. In other embodiments of the invention, spatial variation may be due to other factors.

Figure 3:
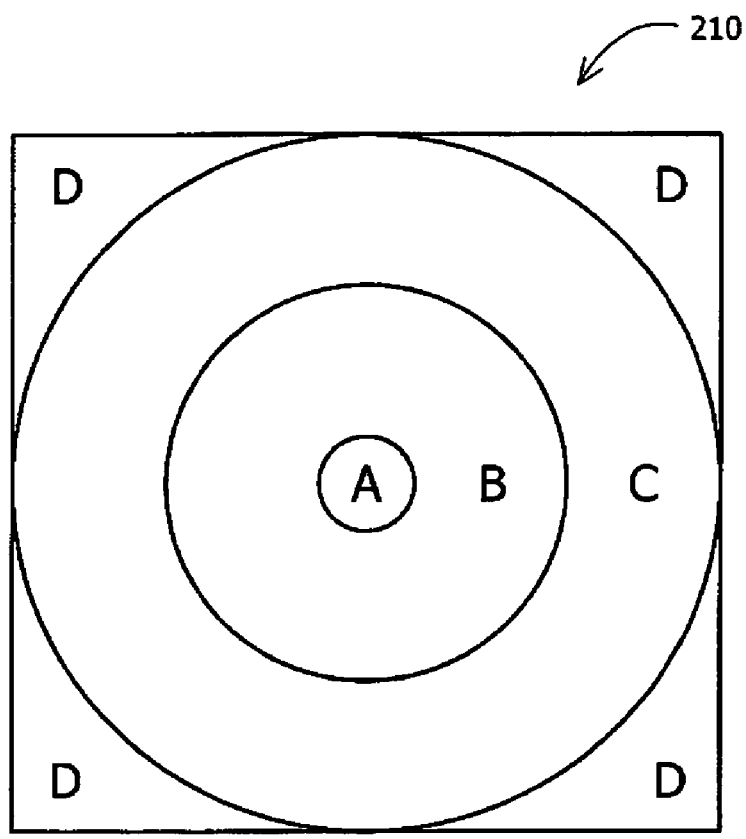
FIG. 3 is a schematic illustration of an image frame divided into sub-regions according to an embodiment of the present invention.

In some embodiments of the invention, the imaging area may, for example, be divided into one or more sub-regions, where different reduction ratios may be applied to each sub-region. FIG. 3 schematically shows a frame 210 divided into 4 sub-regions: A-D. In one embodiment of the invention, for example, sub-regions A and D may contain no relevant image data and may therefore not be included in a reduced image and may not be, for example, transmitted, stored, processed, etc. Sub-region B may be, for example, considered a low-resolution area and therefore may be, for example, reduced minimally or not at all. Sub-region C may be for example, considered a high-resolution area, so that a large part of the reduction may, for example, occur in sub-region B. Other suitable number of sub-regions may be used as well. In one embodiment of the invention, frame 210 may be divided into more or less than 4 sub-regions. In some embodiments of the present invention, the reduction rate of each sub-region and each sub-region's spatial area may be determined, for example, based on an overall desired reduction rate desired. Other suitable methods of dividing frame 210 into sub-regions may be implemented.

In some embodiments of the invention, reduction may be accomplished with minimal processing power by diluting a captured data, for example by selecting only a pattern of pixels for transmission. Such creation of a selection of data, where the selection is typically less data than the original data, may be, for example, performed according to a dilution pattern. Dilution patterns may be based, for example, on the good correlation known to exist between data transmitted from neighboring pixels. While this may result in some loss of quality in the resulting image, proper selection of pixels according to a suitable dilution pattern, together with proper reconstruction of the diluted image, may preserve the quality of the transmitted image and rehabilitate the image to lossless or near-lossless condition. Other bases for dilution methods may be used, and other reduction methods such as known compression algorithms may be used.

In one exemplary embodiment of the invention, the transmitted data may be image data, for example, a rectangular image of 512×512 pixels. It may be desired to reduce the size of the captured image to, for example, a 256×256 pixel image. Other suitable image pixel sizes and reduced image sizes may be used. In one example, the region of the relevant image data (for example region B and C in FIG. 3) may be known to be bounded in, for example, a disk having, for example, an outer diameter of 512 pixels and an inner diameter of, for example, 164 pixels (=0.32*512). The region containing the relevant image data may be defined by the properties the optical system used, or due to other factors. Other defined regions, number of pixels, and other shapes may be implemented as well. The defined sub-regions may, for example, differ in image quality, image resolution, zooming, type of information, etc. In one embodiment of the present invention, the difference in type of information sampled may be due, for example, to a sensor having an optical output, for example, displayed on one section of a viewing window of an in-vivo imaging device, so that the imaging device may capture an image of a lumen together with the output of a sensor on the same image frame. Other suitable types of information may be sampled as well. An area with relevant image data may be in one example of the present invention, divided into sub-regions B and C in FIG. 3. B may be considered in one embodiment of the invention, for example, a low-resolution sub-region as compared to sub-region C that may be considered, for example, high-resolution sub-region. In one example, pixels in sub-regions A and D may be known to contain no relevant image data and may not be included in the diluted and/or compressed image. In one exemplary embodiment, all pixels in sub-region B, for example, may be included (no dilution in sub-region B), while for example, only every fourth pixel in sub-region C may be included in the diluted image. Other methods of reducing data in sub-region C, for example, by known compression methods, may be used. In one exemplary embodiment of the invention, an alternate dilution pattern may be used. For example, a dilution pattern that repeats itself, for example, every four rows, may be used. One example of such a pattern may be a pattern where, no pixels may be transmitted from a first row, every fourth pixel may be transmitted from each of the next two rows, and every second pixel may be transmitted from the fourth row. Other suitable diluting patterns suitable for various pixels grids may be implemented. In another embodiment, sub-region B may also be diluted and/or compressed. The limits, area, boundaries and/or size of the sub-regions may be defined based on the reduced data size required. For example, the size and/or diameter of sub-regions B and C may be, for example, defined based on the resultant reduced data size required. In one embodiment of the present invention, the limits of the one or more sub-regions and the reduction ratio in each sub-region may be, for example, preset, for example, during the manufacturing process of the imager and/or of the assembled device by, for example, the data reduction circuit 44. In other embodiments, the limits and reduction ratios may be preset by other components or directly by, for example, the imager. In yet other embodiments, the limits and reduction ratio may not be preset, and may be defined, for example, in real time during an imaging session.

In one exemplary embodiment, in order for a dilution pattern to reduce a 512×512 pixel image to, for example, a 256×256 pixel image the diameter of sub-region B may be, for example, determined by the following equations:

Define:
dA—diameter of sub-region A;
dB—diameter of sub-region B;
dC—diameter of sub-region C;
nA—number of pixels in sub-region A;
nB—number of pixels in sub-region B;
nC—number of pixels in sub-region C;
and define ratios:

$$Ra=dA/dC;$$

$$Rb=dB/dC.$$

In one example of the present invention, sub-region A, B, C may be bounded by circular perimeters and the number of pixels in each sub-region may be expressed by the following equations:

$$nA=dC^2*Ra^2*\Pi/4;$$

$$nB=dC^2*Rb^2*\Pi/4-nA;$$

$$nC=dC^2*\Pi/4-nA-nB.$$

Define:
DR—overall dilution ratio;
DRc—dilution ratio in sub-region C.
The reduced data size may be defined by:

$$dC^2/DR=nB+nC/DRc.$$

Where $dC^2/DR$ is the resultant number of pixels in image frame 210 after dilution (area of rectangular image frame 210 divided by the overall dilution ratio) and nC*DRc may be the number of pixels in region C after dilution.

It may therefore follow that the diameter of sub-region B may be defined by the following equation:

$$dB=((4/pi)*Ra^2/DR-1/DRc)/(1-1/DRc).$$

The above set of equations is just by way of example, according to the sub-regions defined in FIG. 3, other number of sub-regions, shapes of sub-regions, and ratios may be used and compression may be used instead or in addition to dilution. In other embodiments of the invention, more than one sub-region may be diluted and/or compressed using more than one ratio. In one embodiment of the invention, the dilution and/or compression ratio may be a function of the diameter of each sub-region, for example, the dilution ratio may, for example, increase linearly with increasing diameter. In other embodiments, more processor intensive methods such as known compression methods, for example, JPEG or other suitable compression methods may be used instead of or in partially instead of dilution. In yet another embodiment of the invention compression methods may be used together with dilution, for example a diluted image may be subsequently compressed using any suitable compression methods known in the art. Other operations or series of operations may be used.

In other embodiments of the invention, the limitations of different sub-regions, for example, sub-regions A, B, C, and D may be determined based on the resolution and/or other information of the captured image and the dilution ratio in each sub-region may be determined based on the pre-defined spatial areas and the resultant diluted image size desired. Different dilution ratios may be used for different regions or sub-regions.

When employing known compression algorithms, the size of the reduced image may not be known prior to the execution of the algorithm. For example, the size of the reduced image may depend on the information in the image due to be compressed. In some embodiments of the present invention, the resulting size of the compressed image may exceed the size that may be transmitted through a transmission channel that may have a limited bandwidth. In one embodiment of the present invention, the size of the compressed image may be monitored by a feedback algorithm that may alter, for example, a parameter of the compression algorithm as a function of the forecasted size of the final compressed image. As such, for example, the compression ratio may be altered during a compression procedure. In one embodiment of the present invention, the compression algorithm may be set to, for example, a near loss-less compression at the beginning of the compression procedure. After, for example, a defined number of lines of image data may have been compressed; the size of the compressed data may be compared to a predefined threshold. If the current size of the compressed data may exceed a defined threshold, the compression algorithm may switch to, for example, a lossy compression when compressing the subsequent lines of image data. As such, the image quality in the area that was first compressed may be better than the image quality in an area that was compressed toward the end.

In one embodiment of the invention, the compression algorithm may include instructions to begin compression close to a region of interest, for example, near the center of the image frame so that high quality compression may be insured near a region of interest. Other suitable methods of compression may be implemented. Compression may be implemented per line of image data. For example a first line of image data may be stored, for example in memory 77, a compression algorithm may be implemented to compress that line of data, the compressed line of data may then, for example, be transmitted, and the procedure may be repeated for the next line of data. The first line of data to be compressed may be the top line, the middle line, or any other suitable preset line, and the order of the lines to be compressed may be in any preset order. In other embodiments of the present invention, other suitable methods of compression may be implemented, for example, compression including more or less data to be compressed at a time. In other embodiments of the present invention, compression may be implemented on a set of image data that may not be defined by lines of image data. For example, a spiral path beginning at, for example, the center of an image may be defined. Compression may be implemented on preset number of pixels along the path at a time. Other spatial patterns of compression may be used.

The compressed and/or diluted image may later be processed, for example, reconstructed to its original data size. In one embodiment of the invention, processing or partial processing of a reduced image may be performed in, for example, the receiving unit 12 with optional receiving unit processor 51 and/or data processor 14. In one embodiment of the invention, interpolation may be performed to, for example, fill in gaps between data. Interpolation may include, for example, linear, quadratic, bi-cubic, polynomial, weighted average, or other suitable interpolation. Edge information may be used to weight differently each of the samples. For example, pixels along directions with high gradient (possibly close to an edge) may, for example, not be included in interpolation. Other suitable weighting factors may be included. In one embodiment of the invention, intensity may be calculated and used during interpolation for maintaining the ratio between color and intensity during interpolation. Other suitable methods of filling in the gaps may be implemented. After, for example, interpolation or post-processing may be performed on interpolated data, for example to enhance a reconstructed image. Post-processing may, for example, include image sharpening, color suppression, intensity adjustment, convolution or a median filter. Other suitable post-processing techniques may be implemented.

In one embodiment of the invention, a distorted ring shaped panoramic image 214 (FIG. 2B) may be converted to a rectangular shaped non-distorted image using algorithms well know in the art. The conversion may include other suitable operations for image manipulation and/or image enhancement, performed before and/or after transmission of the image by, for example, transmitter 41 to receiving unit 12, or may be performed in data processor 14.

In an alternate embodiment of the invention, the spatial variation in, for example, resolution may be due to two or more images with separate optical paths captured in different areas on a single frame. In such an embodiment it may be desirable to employ different compression or dilution ratios, and/or compression algorithms or dilution patterns to for example the different images captured on a single image frame. In one example, the spatial dilution ratio may depend on properties of the separate optical paths. In other examples, the dilution rate and pattern may be dependent on other suitable properties.

Figure 4:
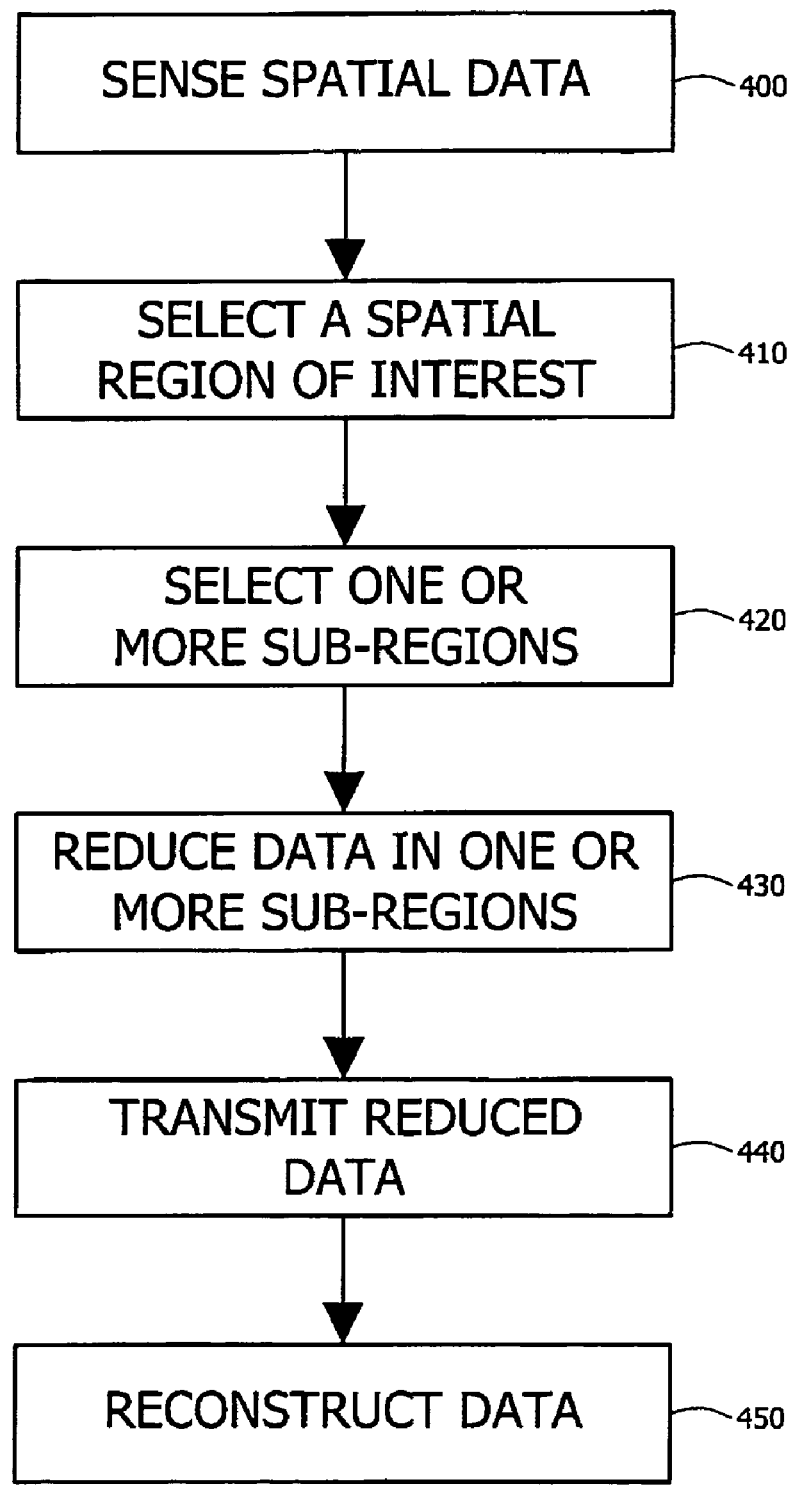
FIG. 4 is a flow chart describing a method for reducing the size of data, according to some embodiments of the present invention.

Reference is now made to FIG. 4, showing a flow chart of a method for in-vivo imaging according to some embodiments of the present invention. In some embodiments of the invention, an in-vivo imaging device, for example device 100, may sense spatial data (block 400), for example, image data. In block 410, a preset region of interest in, for example, an area within an image frame may be selected for transmission, storing, processing, etc. In block 420, one or more preset sub-regions may be selected. The preset division of sub-regions may be based on certain properties, for example, resolution, lighting, type of data, etc. Each sub-region may be reduced (e.g. diluted, and/or compressed) based on a preset reduction ratio (block 430). For example, each sub-region may be reduced by a defined compression ratio and/or dilution pattern described herein. Other suitable spatially reduction means may be implemented. The preset reduction ratio in each sub-region may be constant or may be a function of spatial position of data. In one exemplary embodiment, some sub-regions may not be reduced (e.g., may have a reduction ratio of 1). In block 440, the selected spatial region, for example, of the image frame in a reduced form may be transmitted, for example, by wireless communication. In other embodiments, the reduced data from the selected spatial region of interest may be further compressed with known methods before transmission, may be stored, transmitted by wire connection, or otherwise further processed. Reduced data may be, for example, received by a data receiving unit and/or a recorder 12 that may be positioned close to or worn on a subject. A data receiving unit and/or recorder 12 may of course take other suitable configurations. The data receiving unit and/or recorder 12 may transfer the received information to a stationary computing device, such as a workstation or personal computer, where the data may be further analyzed, stored, and/or displayed to a user. In other embodiments, each of the various components need not be required; for example, an internal device may transmit or otherwise transfer (e.g., by wire) information directly to a viewing or processing system. In some embodiments of the present invention, compression may, for example, be performed on diluted image data prior to transmission. In other embodiments of the invention, some regions may, for example be diluted whereas others may be compressed.

In block 450 reduced and/or diluted data may be reconstructed, for example, using methods described herein. Typically the reconstruction may be done in the data receiving unit 12 or in the computing device. The reconstruction may include various processing methods to reconstruct diluted pixels and may also include converting and/or correcting a distorted image as may be described herein. Other operations or series of operations may be used.

While the invention has been described with respect to a limited number of embodiments, it will be appreciated that many variations, modifications and other applications of the invention may be made. Embodiments of the present invention may include other apparatuses for performing the operations herein. Such apparatuses may integrate the elements discussed, or may comprise alternative components to carry out the same purpose. It will be appreciated by persons skilled in the art that the appended claims are intended to cover all such modifications and changes as fall within the true spirit of the invention.

The invention claimed is:

1. A method for reducing image data, the method comprising:
    selecting image data from a preset spatial region on an image frame; and
    reducing data in said preset spatial region by;
        selecting a first sub-region in said preset spatial region;
        reducing data in the first sub-region by applying a first reduction ratio;
        selecting a second sub-region in said preset region; and
        reducing data in the second sub-region by applying a second reduction ratio.

2. The method according to claim 1 wherein the reducing is according to a dilution pattern.

3. The method according to claim 2 wherein the dilution comprises selecting every fourth datum.

4. The method according to claim 1 wherein dilution is by applying a constant reduction ratio.

5. The method according to claim 1 comprising compressing data in said preset spatial region.

6. The method according to claim 5 wherein compressing is by JPEG compression.

7. The method according to claim 1 comprising:
    transmitting the data from a preset spatial region; and
    reconstructing the transmitted data.

8. The method according to claim 1 wherein the spatial data has a spatially varying resolution.

9. The method according to claim 1 wherein image data is captured by a CMOS imager.

10. The method according to claim 1 wherein image data is captured by an autonomous in-vivo imaging device.

11. A method for diluting an image frame having spatially varying resolution, the method comprising:
selecting a preset region in the image frame;
selecting a first sub-region in said region, said first sub-region having a first selected range of resolution;
selecting a second sub-region in said region, said second sub-region having a second selected range of resolution;
diluting data in said first sub-region by a first dilution ratio; and
diluting data in said second sub-region by a second dilution ratio.

12. The method according to claim 11 comprising transmitting data in said region.

13. The method according to claim 11 wherein diluting is by a selected dilution pattern.

14. The method according to claim 11 comprising reconstructing the data in said region wherein the data is diluted data.

15. A method for reducing image data, the method comprising:
selecting a first sub-region in an image frame;
reducing data in the first sub-region by applying a first reduction ratio;
selecting a second sub-region in said image frame; and
reducing data in the second sub-region by applying a second reduction ratio.

16. The method according to claim 15 wherein said sub-region is selected from a preset spatial region in the image frame.

17. The method according to claim 16 comprising compressing data in said preset spatial region.

18. The method according to claim 17 wherein compressing is by JPEG compression.

19. The method according to claim 16 wherein the data in the spatial region has a spatially varying resolution.

20. The method according to claim 15 wherein the reducing is according to a dilution pattern.

21. The method according to claim 15 wherein dilution is by applying a constant reduction ratio.

22. The method according to claim 15 wherein the dilution comprises selecting every fourth datum.

23. The method according to claim 15 comprising:
transmitting the reduced data; and
reconstructing the transmitted data.

24. The method according to claim 15 wherein image data is captured by a CMOS imager.

25. The method according to claim 15 wherein image data is captured by an autonomous in-vivo imaging device.

* * * * *